United States Patent
Bjaerum et al.

(10) Patent No.: US 6,652,462 B2
(45) Date of Patent: Nov. 25, 2003

(54) ULTRASOUND DISPLAY OF MOVEMENT PARAMETER GRADIENTS

(75) Inventors: Steinar Bjaerum, Horten (NO); Bjorn Olstad, Stathelle (NO); Kjell Kristoffersen, Oslo (NO)

(73) Assignee: GE Medical Systems Global Technology Company, LLC., Waukesha, WI (US)

( * ) Notice: Subject to any disclaimer, the term of this patent is extended or adjusted under 35 U.S.C. 154(b) by 0 days.

(21) Appl. No.: 10/064,033

(22) Filed: Jun. 4, 2002

(65) Prior Publication Data

US 2003/0013957 A1 Jan. 16, 2003

Related U.S. Application Data

(60) Provisional application No. 60/297,572, filed on Jun. 12, 2001.

(51) Int. Cl.[7] .................................................. A61B 8/02
(52) U.S. Cl. ........................................ 600/450; 600/453
(58) Field of Search ................................ 600/407, 437, 600/438, 440–447, 449–471; 382/132, 154, 128; 128/916; 73/620–633; 367/7, 11, 130, 138

(56) References Cited

U.S. PATENT DOCUMENTS

| | | |
|---|---|---|
| 5,615,680 A | 4/1997 | Sano |
| 5,820,561 A | 10/1998 | Olstad et al. |
| 6,110,119 A * | 8/2000 | Hall ........................... 600/455 |
| 6,120,451 A * | 9/2000 | Washburn et al. .......... 600/454 |

* cited by examiner

Primary Examiner—Ali M. Imam
(74) Attorney, Agent, or Firm—McAndrews, Held & Malloy, Ltd.; Peter J. Vogel; Michael A. Dellapenna

(57) ABSTRACT

An ultrasound machine is disclosed that displays a color representation of moving structure, such as a cardiac wall tissue, within a region of interest on a monitor. The color representation is generated by displaying color hues corresponding to a movement parameter of the structure, such as velocity or strain rate in such a manner as to provide for quantitative visualization of movement parameter gradients. The movement parameter is mapped to the color hues by apparatus comprising a user interface that allows the user to input color band resolution and a local range of relative parameter values. A front-end generates received signals in response to ultrasound waves. A Doppler processor generates a set of parameter signals representing absolute values of the movement parameter within the structure. A set of color characteristic signals is generated by a display processor in response to the set of parameter signals and to a user-defined local range of relative parameter values. The color characteristic signals, representative of the gradient of the movement parameter of the moving structure, are displayed as a color representation on a monitor.

20 Claims, 6 Drawing Sheets

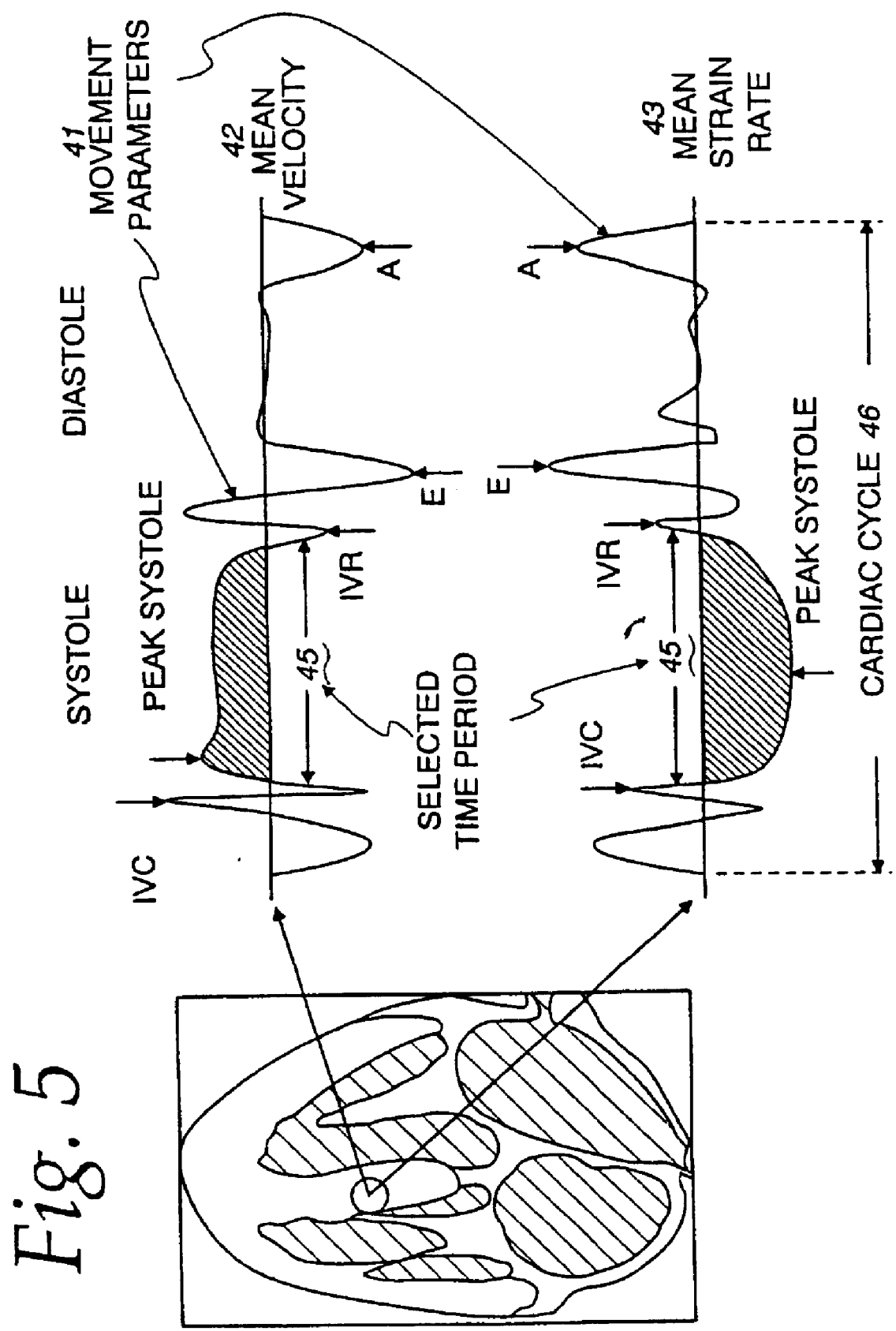

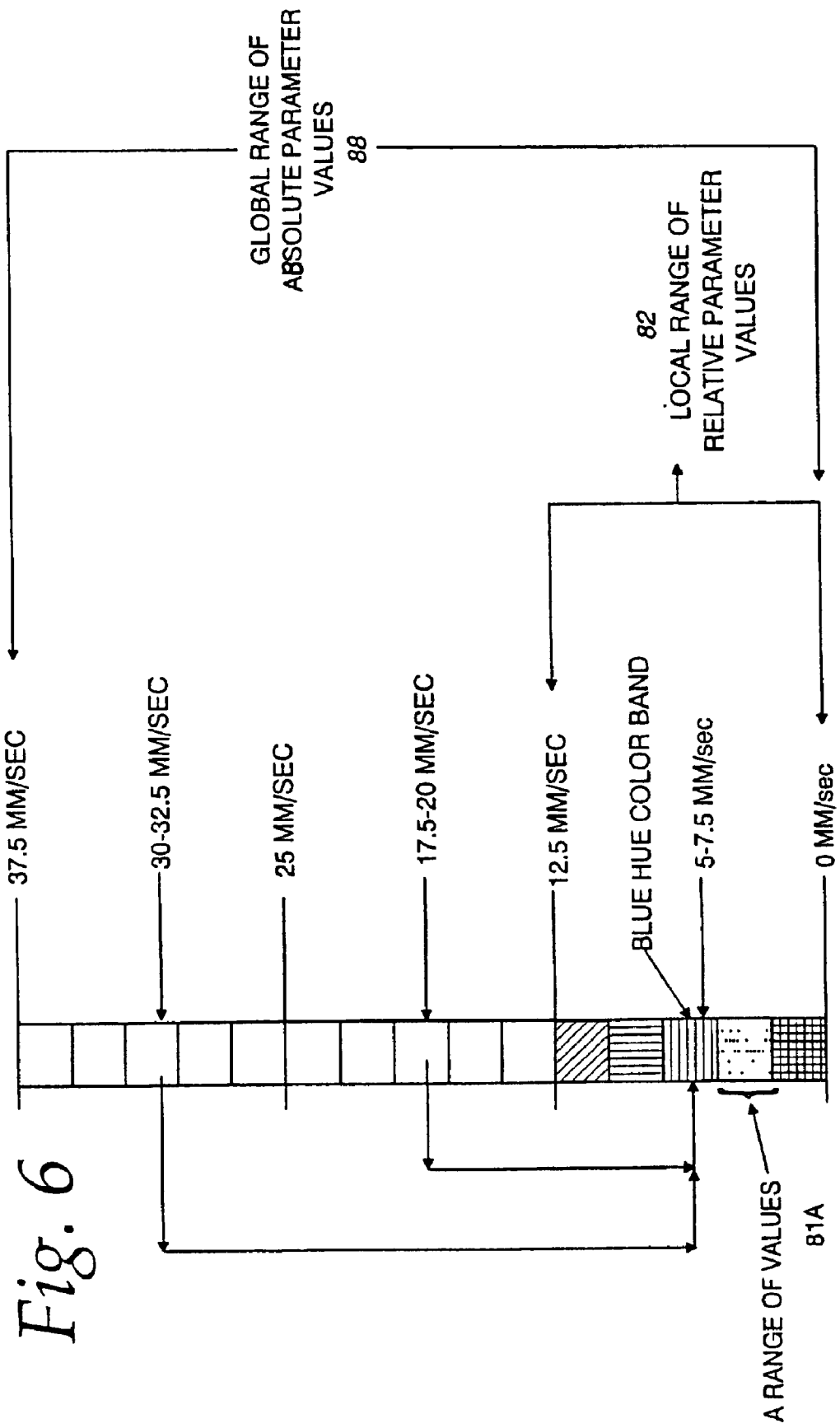

ULTRASOUND DISPLAY OF MOVEMENT PARAMETER GRADIENTS

CROSS REFERENCE TO RELATED APPLICATIONS

The applicants claimed priority based on provisional application No. 60/297,572 filed Jun. 12, 2001 in the names of Bjorn Olstad, Steinar Bjaerum, and Kjell Kristoffersen.

BACKGROUND OF INVENTION

Certain embodiments of the present invention relate to an ultrasound machine for displaying an image of moving structure. More particularly, certain embodiments relate to providing real-time visualization of movement parameter gradients in such an image.

Echocardiography is a branch of the ultrasound field that is currently a mixture of subjective image assessment and extraction of key quantitative parameters. Evaluation of cardiac wall function has been hampered by a lack of well-established parameters that may be used to increase the accuracy and objectivity in the assessment of, for example, coronary artery diseases. Stress echo is such an example. It has been shown that the subjective part of wall motion scoring in stress echo is highly dependent on user training and experience. It has also been shown that inter-observer variability between echo-centers is unacceptably high due to the subjective nature of the wall motion assessment.

Much technical and clinical research has focused on the problem and has aimed at defining and validating quantitative parameters. Encouraging clinical validation studies have been reported, which indicate a set of new potential parameters that may be used to increase objectivity and accuracy in the diagnosis of, for instance, coronary artery diseases. Many of the new parameters have been difficult or impossible to assess directly by visual inspection of the ultrasound images generated in real-time. Often, processing-intensive mathematical calculation of the parameter gradient is required. In other situations, quantification has required a post-processing step with tedious, manual analysis to extract the necessary parameters.

Much of the prior art describes techniques for color mapping estimated imaging parameters such as tissue velocity and strain rate. A fixed mapping of a continuous range of color hues is typically used to indicate positive velocities or strain rates and a second fixed mapping of a continuous range of color hues is used to indicate negative velocities or strain rates.

However, color schemes in prior art are not well suited for visual determination of other parameters such as velocity gradients or motion gradients. Typically, a Nyquist velocity and associated pulse repetition frequency is set in order to avoid aliasing. A problem in parasternal views, for example, is that there may be a large range of actual velocities or actual motion values. But a localized myocardial gradient, for example, may occupy only a small fraction of the overall velocity or motion range. Typical prior art color encoding of, for example, a 2-dimensional sector display may, therefore, not be capable of actually separating the velocities or motion values between, for example, endocardium and epicardium with clearly differentiating colors. Quantitative assessment through visualization of parameters such as velocity and motion gradients from localized areas in 2-D images has been difficult, even in lucky situations, with an optimum spread of measured imaging parameters. It has often been necessary to resort to post-processing techniques and manual extraction of the digital information used in the color encoding for estimation of parameter gradients. In other scenarios, processing-intensive mathematical calculations of the parameter gradient are required.

For example, U.S. Pat. No. 5,615,680 (Sano, issued Apr. 1, 1997) describes real-time calculating of velocity gradients (average slopes) between a plurality of regions using a least squares technique and then displaying brightness levels to indicate gradients between the regions. According to Col. 18, lines 20–23 and FIG. 28, a red tone is allocated to segments whose associated average slopes are lower than a threshold, and a blue tone is allocated to segments whose associated average slopes exceed the threshold.

U.S. Pat. No. 5,820,561 (Olstad, et al., issued Oct. 13, 1998) describes display of velocities in M-mode polygons. A user may view velocity variations to attempt to determine velocity gradients between the polygons (Col. 5, lines 42–54).

None of the foregoing patents, however, describe or suggest user control to set a desired parameter range of values and a desired color legend so that gradients may be readily estimated by a user.

A need exists for a simple, yet robust approach to easily visualize gradients of tissue motion parameters, such as strain rate, in a two-dimensional ultrasound image.

SUMMARY OF INVENTION

An embodiment of the present invention provides an ultrasound system for generating an image responsive to gradients of motion parameters that are representative of tissue motion.

An apparatus is provided in an ultrasound machine that is arranged to generate an image responsive to moving structure within a region of interest of a subject. The movement of the structure is defined by a movement parameter. A user of the machine may visually estimate gradients of the movement parameter of the structure by displaying color hues corresponding to ranges of values of the movement parameter. In such an environment the apparatus for displaying the color hues comprises a user interface to enable the user to define a plurality of ranges of values of the movement parameter and to assign selected color hues to the ranges. A front-end is arranged to generate transmitted signals into the structure and then to generate received signals in response to ultrasound waves backscattered from the structure. A processor is responsive to the received signals to generate a set of parameter signals representing values of the movement parameter within the structure and within the plurality of ranges of the movement parameter during a time period. A display is responsive to the set of parameter signals to display an image of the structure within the region of interest with color hues corresponding to the plurality of ranges of values of the movement parameter. A color legend comprising the color hues and indicating a correspondence between the ranges of values of the movement parameter and the color hues is also displayed.

A method is also provided in an ultrasound machine that is arranged to generate an image responsive to moving structure within a region of interest of a subject. The movement of the structure is defined by a movement parameter. Gradients of the movement parameter of the structure may be visually estimated by displaying color hues corresponding to ranges of values of the movement parameter. In such an environment, the method for displaying the color hues comprises enabling a user to define a plurality of ranges of values of the movement parameter and assigning selected color hues to the ranges. Signals are transmitted into the structure and then received in response to ultrasound waves backscattered from the structure within the region of interest over a time period. A set of parameter signals representing values of the movement parameter within the structure and within the plurality of ranges of the movement parameter is generated in response to the received signals. The image of the structure is displayed within the region of interest represented by the color hues corresponding to the plurality of ranges of values of the movement parameter. A color legend comprising the color hues and indicating a correspondence between the ranges of values of the movement parameter and the color hues is also displayed.

Certain embodiments of the present invention afford an approach for visualizing parameter gradients of moving structure on a color display in real-time with a degree of convenience and accuracy previously unattainable in the prior art without requiring a real-time mathematical calculation of the parameter gradient.

BRIEF DESCRIPTION OF DRAWINGS

FIG. 5 illustrates typical velocity and strain rate profiles as a function time, measured longitudinally in an apical view of the heart by the machine in FIG. 1 in accordance with an embodiment of the present invention.

FIG. 6 is a graphic illustration showing how the color-encoding of the method in FIG. 2 collapses several widely different ranges of absolute velocity values into a single relative range of velocity values in accordance with an embodiment of the present invention.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION

An embodiment of the present invention enables quantitative visualization of parameter gradients within moving structure. As used herein, "structure" means non-liquid and non-gas matter, such as cardiac wall tissue. An embodiment of the present invention offers improved, real-time visualization and assessment of wall tissue function. The moving structure is characterized by a movement parameter, which means a parameter derived from movement of the structure, such as velocity or strain rate.

Figure 1:
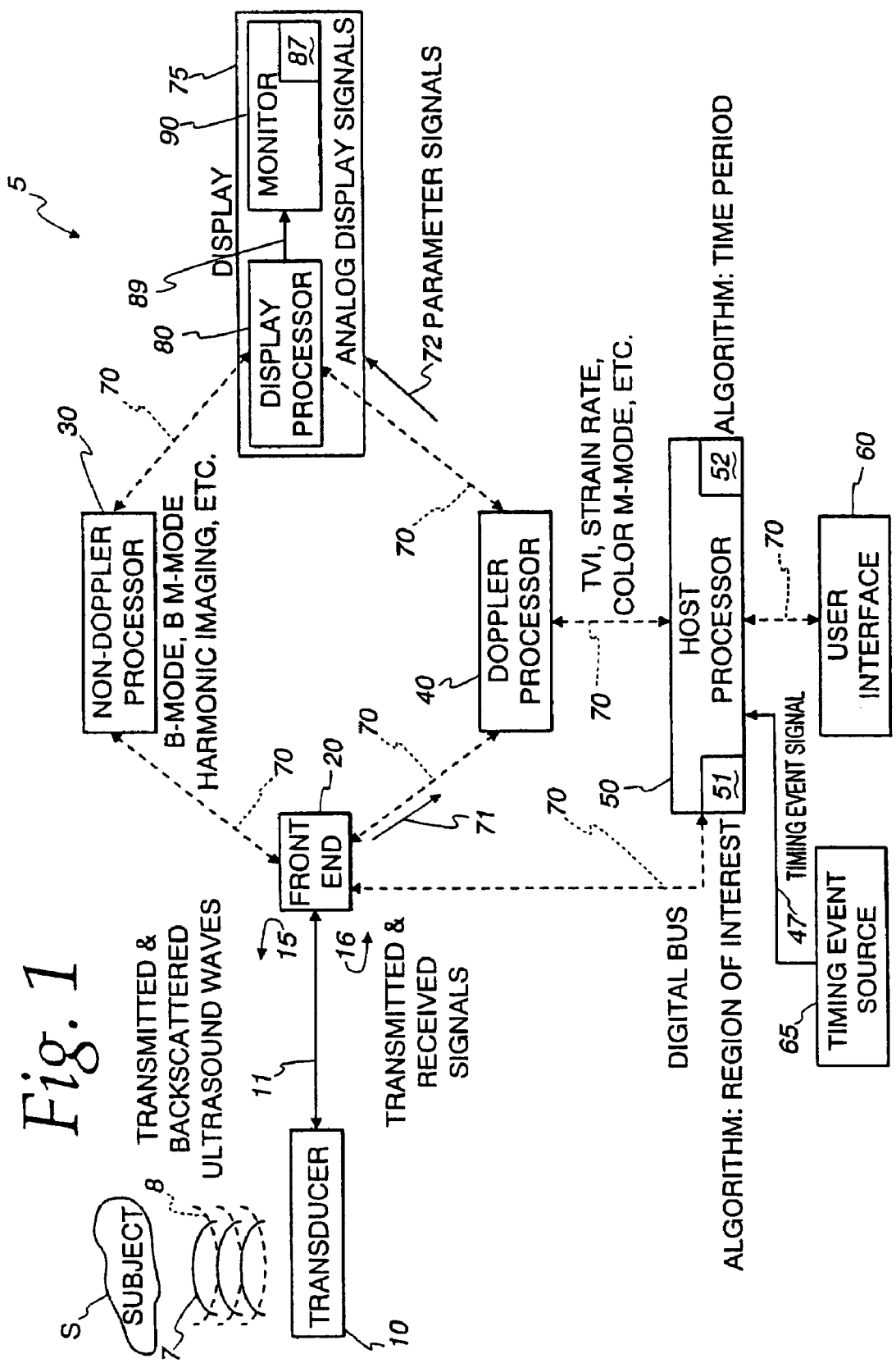
FIG. 1 is a schematic block diagram of an ultrasound machine in accordance with an embodiment of the present invention.

Referring to FIG. 1, a user interface 60 allows commands to be input by a user to the ultrasound machine 5, such as a range of values and a color band resolution. User interface 60 comprises a keyboard, mouse, switches, knobs, buttons, track ball, and on screen menus (not shown).

A transducer 10 is used to transmit ultrasound waves 7 (solid curves in FIG. 1) into a subject S by converting electrical analog signals 15 to ultrasonic energy and to receive ultrasound waves 8 (dashed curves in FIG. 1) backscattered from the subject by converting ultrasonic energy to analog electrical signals 16.

A front-end 20 comprising a receiver, transmitter, and beamformer, is used to create the necessary transmitted waveforms, beam patterns and receiver filtering techniques that are required for the various imaging modes. Front-end 20 performs the functions by converting digital data to analog data and vice versa. Front-end 20 interfaces at an analog interface 11 to transducer 10 and interfaces at a digital interface over a digital bus 70 to a non-Doppler processor 30 and a Doppler processor 40 and a host processor 50. Digital bus 70 may comprise several digital sub-buses, each sub-bus having its own unique configuration and providing digital data interfaces to various parts of the ultrasound machine 5.

Non-Doppler processor 30 comprises amplitude detection functions and data compression functions used for imaging modes such as B-mode, B M-mode, and harmonic imaging. Doppler processor 40 comprises clutter filtering functions and movement parameter estimation functions used for imaging modes such as tissue velocity imaging (TVI), strain rate imaging (SRI), and color M-mode. The two processors, 30 and 40, accept digital data from the front-end 20, process the data into estimated values of amplitude and estimated values of movement parameters (such as mean velocity and mean strain rate), and pass the values to a display 75 over digital bus 70. The estimated values may be created using the received signals in frequency bands centered at harmonics or sub-harmonics of the transmitted signals in a manner known to those skilled in the art.

Display 75 comprises scan-conversion functions, color mapping functions, and tissue/flow arbitration functions, performed by a display processor 80 which accepts digital parameter signals 72 from processors 30 and 40, processes, maps, and formats the digital data for display, converts the digital display data to analog display signals 89, and passes the analog display signals 89 to a monitor 90.

Monitor 90 accepts the analog display signals 89 from display processor 80 and displays the resultant image 87 to the user on monitor 90.

Display 75 may take many forms known to those skilled in the art of image display.

Host processor 50 is the main, central processor of the ultrasound machine 5 and interfaces to various other parts of the ultrasound machine 5 through digital bus 70. Digital data and commands may be transmitted and received between the host processor 50 and other various parts of the ultrasound machine 5. The functions performed by processor 50 may be performed by multiple processors or may be integrated into processors 30, 40, or 80, or any combination thereof.

Figure 2:
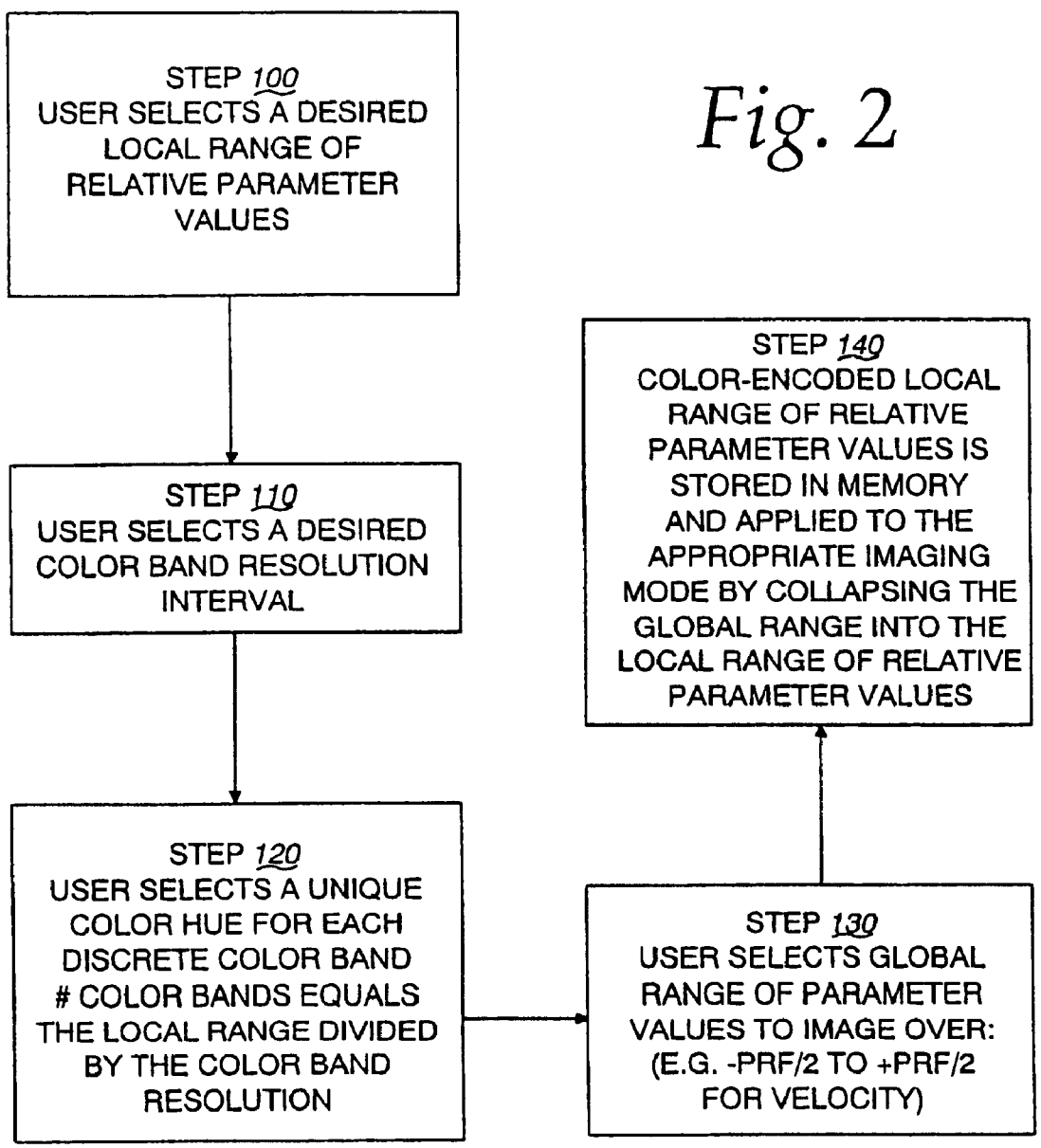
FIG. 2 is a flowchart of a method to color encode a plurality of ranges of the values of the movement parameter based, in part, on a desired parameter resolution in the machine shown in FIG. 1 in accordance with an embodiment of the present invention.

FIG. 2 illustrates the method of how a user defines a color encoded plurality of ranges of the values of the movement parameter to aid in the visualization of quantitative parameter gradients. The color encoding is defined on-line as an integrated feature of the ultrasound machine 5 based on user inputs. As an alternative, such a color encoding may be defined off-line, separate from the ultrasound machine using, for example, a personal computer and then downloading the defined color encoding to the ultrasound machine 5.

Referring to FIG. 2, in step 100 the user selects and defines, through user interface 60, a desired local range of relative parameter values 82 (FIG. 3) in units of the parameter value (e.g. mm/sec for velocity, 1/sec for motion) to be uniquely color encoded as a plurality of ranges of relative values of the movement parameter. The local range of relative parameter values 82 is the range of relative parameter values over which color hues will be encoded before any color hue 84 (FIG. 3) is repeated for a parameter value. The color characteristic legend 85 in FIG. 3 defines a local range of relative parameter values 82 that covers a relative range of 12.5 mm/sec.

Figure 3:
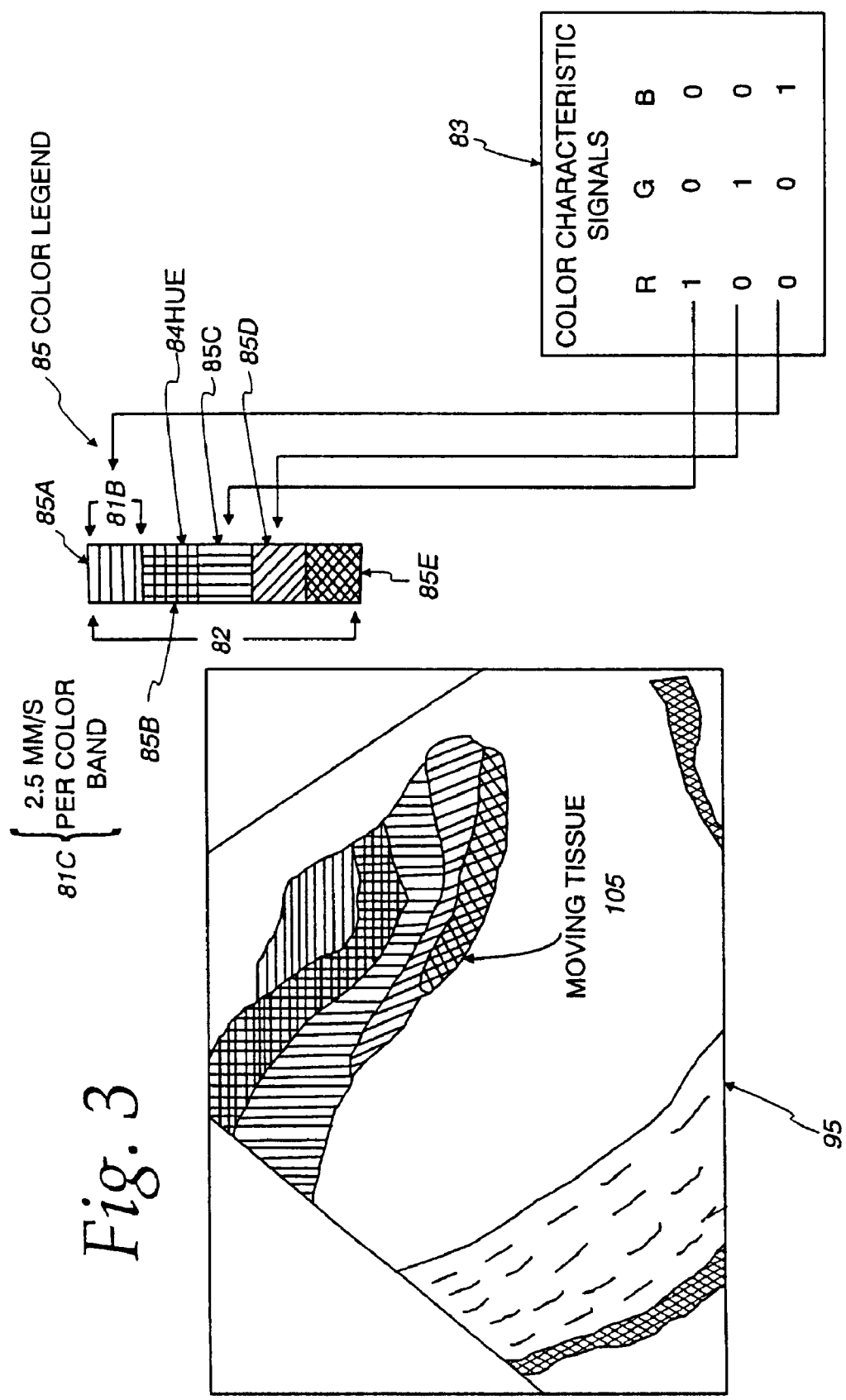
FIG. 3 illustrates an exemplary color representation of velocity gradients using the color encoded plurality of ranges of the values of the movement parameter from the method in FIG. 2 in accordance with an embodiment of the present invention.

In step 110 of FIG. 2, the user selects, through user interface 60, a desired resolution interval 81C of a single, discrete color band 81B, in units of the parameter value (e.g. cm/sec for velocity, 1/sec for motion, etc.). The resolution interval 81C defines a single range of relative values in the plurality of ranges of values 81A (see FIG. 6) of the movement parameter 41 (FIG. 5). For example, the desired resolution required for visualization of the localized myocardial velocity gradient may be 2.5 mm/sec. The color characteristic legend 85 of FIG. 3 shows such a velocity color band 81B with this resolution. The resultant number of color bands in the local parameter value range 82 is then calculated by processor 50 as:

color bands=local range of relative parameter values/color band resolution      [Eqn. 1]

In step 120 of FIG. 2, the user selects, through user interface 60, a unique color hue 84 for each unique, discrete color band 81B in the local range of relative parameter values 82 defined in step 100. The color legend 85 in FIG. 3 illustrates how processor 50 color encodes the local range of relative parameter values 82 based on the user inputs. The color encoding represents a user-defined preset parameter gradient.

In step 130 of FIG. 2, the user selects, through user interface 60, a desired global range of absolute parameter values 88 to image over (see FIG. 6). For example, for tissue velocity imaging (TVI) the user would set the global range of velocity values to image over by adjusting the pulse repetition frequency (PRF) of the imaging mode (−PRF/2 to +PRF/2). The global range of absolute parameter values is based on the expected absolute range of the estimated parameters to be observed in a given scanning application. For example, the global range may be selected to be −37.5 mm/sec to +37.5 mm/sec.

In step 140 of FIG. 2, the color encoded local range of relative parameter values 82 is stored in memory of the display 75 of the ultrasound machine 5 and is applied to the appropriate imaging mode by effectively repeating (or cycling) the color encoded local range of relative parameter values 82 over the global range of absolute parameter values 88 in a contiguous manner. As a result, absolute parameter values over the global range are collapsed into the narrower local range of relative parameter values.

Referring to FIG. 6, for example, if the local range of relative parameter values 82 is 0 to 12.5 mm/sec and the color band resolution 81C is 2.5 mm/sec and a relative velocity value range of 5 mm/sec to 7.5 mm/sec is color encoded with a blue hue, then the blue hue will also color encode absolute velocity value ranges of 17.5 mm/sec to 20.0 mm/sec, 30.0 mm/sec to 32.5 mm/sec and so on (the blue hue encoding is effectively repeated every 12.5 mm/sec over the global range of absolute parameter values 88).

As an alternative, the absolute parameter values in a range of values of, for example, the −37.5 to +37.5 mm/sec range may be color coded and displayed as absolute values (one unique color for each color band over the range of −37.5 to +37.5 mm/sec) instead of color coding and displaying values as relative values as shown in FIG. 6.

Many different color encoding schemes may be created following the method of FIG. 2 where each scheme may have a uniquely defined color band resolution 81B and/or uniquely encoded local range of relative parameter values 82. Different color hues 84 may be encoded as well.

The method of visualizing quantitative parameter gradients in accordance with an embodiment of the present invention is as described below. A user uses transducer 10 to transmit ultrasound energy into the appropriate anatomical structure of subject S, such as cardiac tissue 105 (see FIG. 4 and FIG. 5), of the subject in an imaging mode (such as TVI or SRI) that will yield a desired movement parameter 41 (see FIG. 5) of the anatomical structure 105. As shown in FIG. 5, the movement parameter 41 typically comprises tissue velocity 42 or strain rate 43. The specification herein mainly uses the example of tissue velocity imaging to illustrate embodiments of the present invention. Based on the specification herein, those skilled in the art may also provide an embodiment that employs tissue strain rate and other movement parameters.

Figure 4:
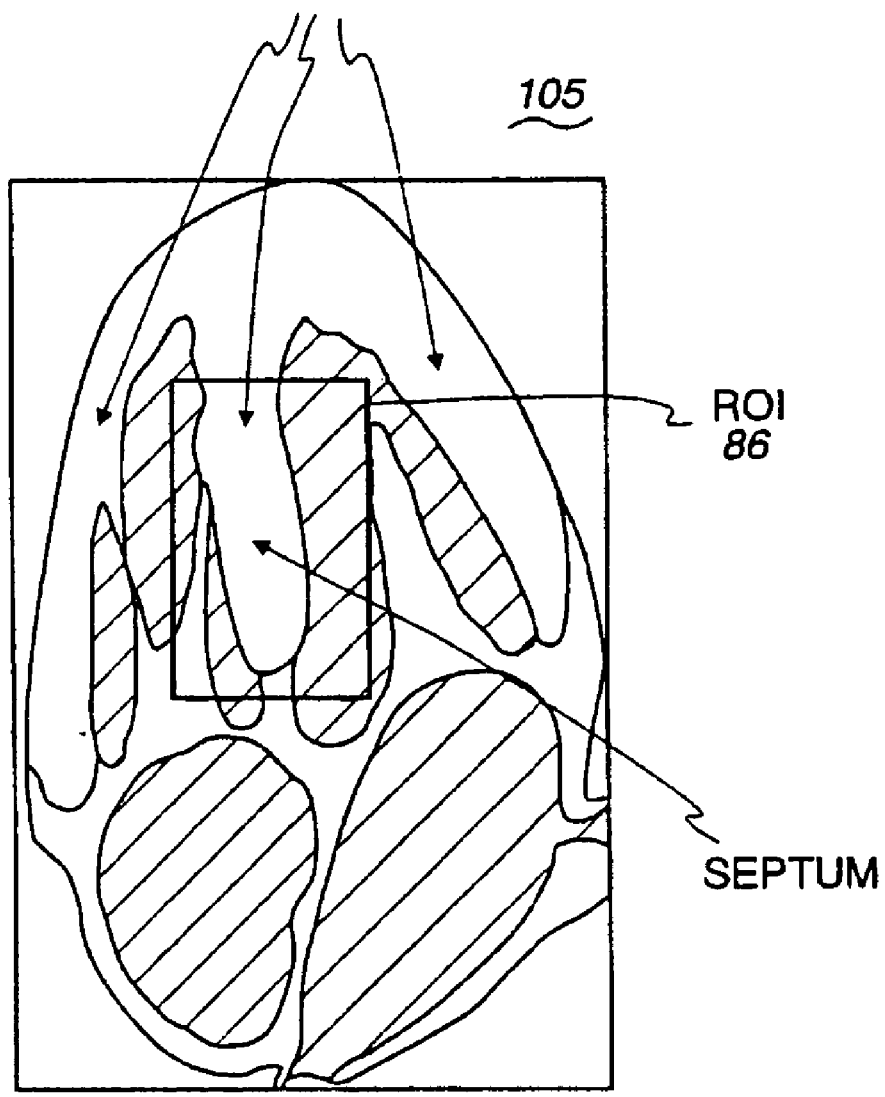
FIG. 4 is a schematic cross-sectional view of the human heart including myocardium tissue bounded by a region of interest (ROI) that is designated by the machine shown in FIG. 1 in accordance with an embodiment of the present invention.

As ultrasound energy is received into transducer 10, signals are received into front-end 20 in response to ultrasound waves 8 backscattered from the structure 105 of subject S over a user-defined region of interest (ROI) 86 (see FIG. 4). The user brings up a scaleable ROI 86 on monitor 90 through the user interface 60 to select a localized area of the image to zoom in on, such as the septum of the heart (see FIG. 4). Designating an ROI may be useful, for example, if the user wants to provoke a good visualization of the myocardial velocity gradient in a specific region. In other similar embodiments, the ROI 86 may be selected automatically or as a combination of manual and automatic methods. For example, an algorithm 51 (see FIG. 1) for automatic identification of an ROI 86 may be designed and embedded in the host processor 50 to separate the myocardium from cavities. Well-known segmentation and thresholding techniques operating on the data of the movement parameter 41 may be used. Alternatively, the ROI may be chosen to cover the entire displayed image 87 if desired (i.e. effectively not employing an ROI).

Received signals 71 are sent from front-end 20 to Doppler processor 40 over digital bus 70. Doppler processor 40 generates many samples of movement parameter signals 72, such as velocity 42 or strain rate 43 using the well-known imaging modes of TVI and SRI based on the received signals 71 within ROI 86. The user selects, through the user interface 60, a desired time interval 45 to process, such as systole, which is a sub-interval of the cardiac cycle 46 (see FIG. 5). The time intervals are determined using well-known timing event sources 65 and signals 47 (FIG. 1) and techniques such as electro-cardiogram (ECG) techniques responsive to an ECG signal and/or analyzing characteristic signatures of the movement parameter 41. It is also possible to derive timing events from signals of other timing event sources such as phonocardiogram, pressure wave, pulse wave, or respiration. Ultrasound modalities such as spectrum Doppler or M-modes may also be used to obtain timing information.

It may be advantageous to select a time period 45 corresponding to a complete cardiac cycle 46 in order to optimize the gradient display for the entire cardiac cycle 46. Another possibility is to limit the time period 45 to the systolic time period in order to display a color representation 95 (FIG. 3)

that is optimized for systolic gradient visualization. Other sub-intervals of the cardiac cycle 46 may also be applied. FIG. 5 illustrates typical velocity and strain rate profiles which may be segmented into desired time periods based on profile features. For reference, the profiles in FIG. 5 are annotated with the times corresponding to: IVC=isovolumetric contraction, IVR=isovolumetric relaxation, E=early diastolic velocity, and A=late diastolic velocity. In other possible embodiments, the time interval may be selected automatically or as a combination of manual and automatic methods. For example, the time period 45 may be determined automatically with an algorithm 52 (see FIG. 1) embedded in host processor 50. The algorithm 52 may use well-known techniques of analyzing the profiles of the movement parameter 41, as shown in FIG. 5, looking for key profile signature characteristics and defining a time period 45 based on the characteristics or, similarly, analyzing an ECG signal. Alternatively, a time interval may not be selected and processing is not limited to any particular segment of the cardiac cycle or multiple cardiac cycles (i.e. the display is continuously updated, independent of the cardiac cycle).

The values of the movement parameter 41 are sent from Doppler processor 40 to display processor 80. The previously defined, color-encoded, local range of relative parameter values 82 is used by display processor 80 as a mapping function between the values of the movement parameter 41 and the discrete color hues 84 in the color legend 85 (see FIG. 3). Therefore, the color-encoded local range of relative parameter values 82 is simply used to map absolute values of the movement parameter to specific, discrete color hues 84 in the color legend 85.

The color encoded local range of relative parameter values 82 is represented digitally in the memory of display 75. The color hues are typically represented in memory as red, green, blue (RGB) values as shown in FIG. 3. The RGB values constitute color characteristic signals 83. The RGB values may be represented as normalized values between 0 and 1, as shown in FIG. 3. Therefore, to represent a perfectly red hue, the RGB values would be (1 0 0). For a perfectly green hue, the RGB values would be (0 1 0), and for blue (0 0 1). Any other color hue may be represented by various combinations of RGB values. For example, if an RGB value is (0.5 0.8 0.3), a combination of unequal parts of red, green, and blue hues each with a different weighting, the result is some new color hue. An RGB combination of (1 1 1) yields a perfectly white hue and an RGB combination of (0 0 0) yields a perfectly black hue.

A color encoded local range of relative parameter values 82 may be quickly defined by the user through user interface 60 allowing the user to change the color band resolution 81C, local range of relative parameter values 82, and color hues 84.

In order to help the user interpret the gradient of the movement parameter, the color legend 85 is displayed on monitor 90 along with a color representation 95 of the movement parameter 41. In a typical TVI mode, the color legend typically employs a continuous range of color hues to indicate positive velocities and a second continuous range of color hues is used to indicate negative velocities. Typically, a red/yellow hues show anatomical motion towards the transducer 10 and blue/green hues show motion away from the transducer 10. However, as shown in FIG. 3, the various cross-hatchings and lines in the color legend 85 represent five discrete ranges of color hues 85A–85E for the user-defined local range of relative velocity values 82. Going from the top of the color legend 85 to the bottom, the color hues transition discretely from blue to yellow to red to green to orange. However, the color hues 84 that make up the color legend 85 may be any discrete combination of hues that provide good discrimination between desired levels of the movement parameter 41. The color encoding, therefore, represents a user-defined, preset parameter gradient and collapses the absolute parameter values into a set of relative discrete bands.

FIG. 3 illustrates an example of applying a color encoded local range of relative parameter values in tissue velocity imaging mode for the myocardium of the heart to create a color representation 95 of the velocity gradient. The absolute velocities are collapsed into a set of discrete color bands (each with a resolution of 2.5 mm/sec), covering a relative velocity range that is typical for endocardium and epicardium tissue. In the example, an anatomical structure colored with 5 of these unique bands will have a total velocity gradient of 5*2.5 mm/s=12.5 mm/s, which indicates 5 ranges of values each having a relative range of 2.5 mm/s. The displayed annotation of "2.5 mm/s" in FIG. 3 indicates a correspondence between the 5 relative ranges of values and 5 different color hues. Bands 85A–85E in color legend 85 each represent a relative range of velocities of 2.5 mm/s less than the preceding band, respectively.

In an embodiment of the present invention the user may effectively shift the color encoded local range of relative parameter values 82 through user interface 60. That is, the encoding of the color bands may be shifted with respect to the absolute values of the global range of parameter values, effectively establishing a new, shifted color encoding. For example, the user may desire to place a specific color hue at the endocardium (towards the blood pool) to make comparisons easier for different measurements. The user may then observe the color hue of the epicardium to compare gradients across the myocardial wall at different locations.

The same methodology may be applied to motion gradients when imaging in strain rate imaging (SRI) mode. The absolute motion values are collapsed into a set of discrete color bands covering a relative motion parameter range that is typical, for example, for endocardium and epicardium motion gradients. The resulting color encoding will, therefore, include color bands that indicate regions with a preset motion gradient. Due to the global motion of the heart in, for example, a parasternal view, it may be necessary to apply tissue tracking techniques to have accurate motion assessments for any anatomical location.

Even though certain embodiments described herein describe a linear encoding technique (i.e. each color band has the same resolution), non-linear techniques may also be applied allowing some color bands to be larger and other color bands to be smaller. As a result, certain parameter bands are emphasized more than others. Other alternative constructs may be implemented as well.

The color encoding methodology may be applied to any imaging mode for any estimated parameter (e.g. velocity, strain rate, power, amplitude, etc.) in order to visualize gradients of that parameter.

In summary, certain embodiments of the present invention afford an approach to visualize gradients of tissue motion parameters, such as tissue velocity or strain rate, in a two-dimensional ultrasound image without having to perform processing-intensive calculations of gradient parameters.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. In an ultrasound machine arranged to generate an image responsive to moving structure within a region of interest of a subject, the movement of the structure being definable by a movement parameter, apparatus for enabling a user of the machine to visually estimate gradients of the movement parameter of the structure by displaying color hues corresponding to ranges of values of the movement parameter, said apparatus comprising:

a user interface arranged to enable the user to define a plurality of ranges of values of the movement parameter and to assign a selected color hue to at least one of the ranges;

a front-end arranged to transmit ultrasound waves into the structure and to generate received signals in response to ultrasound waves backscattered from the structure in the region of interest over a time period;

a processor responsive to the received signals to generate a set of parameter signals representing values of the movement parameter within the structure and within the plurality of ranges during the time period; and a display responsive to the set of parameter signals to display an image of the structure within the region of interest with color hues corresponding to the plurality of ranges of values and, therefore, gradient of the movement parameter, including the selected color hue, and to display a color legend comprising the color hues and indicating a correspondence between the ranges of values and the color hues.

2. The apparatus of claim 1 wherein the color hues are displayed in contiguous areas of the image.

3. The apparatus of claim 2 wherein the color hues are displayed in contiguous color bands within the color legend representing contiguous ranges of values of the movement parameter.

4. The apparatus of claim 1 wherein the user interface enables the user to assign a selected color hue to each of the ranges of values of the movement parameter.

5. The apparatus of claim 1 wherein the user interface is arranged to enable the user to define the plurality of ranges of values of the movement parameter by:

selecting a local range of values of the movement parameter; and selecting a color band resolution within the local range of values.

6. The apparatus of claim 1 wherein the movement parameter comprises one of velocity and strain rate of the structure.

7. The apparatus of claim 1 wherein the structure comprises cardiac tissue.

8. The apparatus of claim 7 wherein the time period comprises at least a portion of a cardiac cycle.

9. The apparatus of claim 8 wherein the user interface is arranged to enable the user to define the time period by defining a portion of the cardiac cycle.

10. The apparatus of claim 8 wherein the time period is automatically determined by an algorithm in the processor responsive to at least one of the set of parameter signals and a signal from a timing event source that generates at least one of an ECG signal, a phonocardiogram signal, a pressure wave signal, a pulse wave signal, and a respiratory signal.

11. In an ultrasound machine arranged to generate an image responsive to moving structure within a region of interest of a subject, the movement of the structure being definable by a movement parameter, a method of enabling a user of the machine to visually estimate gradients of the movement parameter of the structure by displaying color hues corresponding to ranges of values of the movement parameter, said method comprising:

enabling the user to define a plurality of ranges of values of the movement parameter;

enabling the user to assign a selected color hue to at least one of the ranges;

transmitting ultrasound waves into the structure;

generating received signals in response to ultrasound waves backscattered from the structure in the region of interest over a time period;

generating a set of parameter signals representing values of the movement parameter within the structure and within the plurality of ranges during the time period in response to the received signals;

displaying an image of the structure within the region of interest with color hues corresponding to the plurality of ranges of values and, therefore, gradient of the movement parameter, including the selected color hue; and displaying a color legend comprising the color hues and indicating a correspondence between the ranges of values and the color hues.

12. The method of claim 11 wherein said displaying an image comprises displaying the color hues contiguously.

13. The method of claim 12 wherein said displaying a color legend comprises displaying the color hues contiguously as color bands within the color legend representing contiguous ranges of values of the movement parameter.

14. The method of claim 11 wherein said enabling the user to assign a selected color hue comprises enabling the user to assign a selected color hue to each of the ranges of the values of the movement parameter.

15. The method of claim 11 wherein said enabling the user to define a plurality of ranges of values comprises enabling the user to define a plurality of ranges of values of the movement parameter by:

selecting a local range of values of the movement parameter; and selecting a color band resolution within the local range of values.

16. The method of claim 11 wherein the movement parameter comprises one of velocity and strain rate of the structure.

17. The method of claim 11 wherein the structure comprises cardiac tissue.

18. The method of claim 17 wherein the time period comprises at least a portion of a cardiac cycle.

19. The method of claim 18 further comprising enabling the user to define the time period by defining a portion of the cardiac cycle.

20. The method of claim 18 further comprising automatically determining the time period using an algorithm responsive to at least one of the set of parameter values and a timing signal comprising at least one of an ECG signal, a phonocardiogram signal, a pressure wave signal, a pulse wave signal, and a respiratory signal.

* * * * *